US007534573B2

(12) United States Patent
Wesseling

(10) Patent No.: US 7,534,573 B2
(45) Date of Patent: May 19, 2009

(54) METHOD OF IDENTIFYING THERAPEUTIC AGENTS FOR THE TREATMENT OF EPILEPSY

(75) Inventor: John Wesseling, Durham, NC (US)

(73) Assignee: Duke University, Durham, NC (US)

( * ) Notice: Subject to any disclaimer, the term of this patent is extended or adjusted under 35 U.S.C. 154(b) by 701 days.

(21) Appl. No.: 10/738,214

(22) Filed: Dec. 18, 2003

(65) Prior Publication Data

US 2004/0142368 A1 Jul. 22, 2004

Related U.S. Application Data

(60) Provisional application No. 60/433,972, filed on Dec. 18, 2002.

(51) Int. Cl.
*G01N 33/53* (2006.01)
*G01N 33/566* (2006.01)
*C07K 14/00* (2006.01)

(52) U.S. Cl. ......................... 435/7.1; 435/7.2; 436/501; 530/350

(58) Field of Classification Search ....................... None
See application file for complete search history.

(56) References Cited

OTHER PUBLICATIONS

Wallace, R. (2004) Epilepsy: It's no Syn. Epilepsy Curr. 4(5): 188-189.*

Garcia, et al, (2004), J. Med. Genetics. 41:183-186.*

Li et al, "Impairment of synaptic vesicle clustering and of synaptic transmission, and increased seizure propensity, in synapsin I-deficient mice", Proc. Natl. Acad. Sci. USA 92:9235-9239 (1995).

Lynch et al, "The synaptic vesicle protein SV2A is the binding site for the antiepileptic drug levetiracetam", Proc. Natl. Acad. Sci. USA 101(26):9861-9866 (2004).

Yang et al, "Prolonged Exposure to Levetiracetam Reveals a Presynaptic Effect on Neurotransmission", Epilepsia 48(10):1861-1869 (2007).

Wesseling and Lo, "Limit on the Role of Activity in Controlling the Release-Ready Supply of Synaptic Vesicles", The Journal of Neuroscience 22(22):9708-9720 (2002).

Bekkers et al, "Excitatory and inhibitory autaptic currents in isolated hippocampal neurons maintained in cell culture", Proc. Natl. Acad. Sci. USA 88:7834-7838 (1991).

Bartos et al, "Fast synaptic inhibition promotes synchronized gamma oscillations in hippocampal interneuron networks", Proc. Natl. Acad. Sci. USA 99(20):13222-13227 (1991).

Galarreta et al, "Frequency-dependent synaptic depression and the balance of excitation and inhibition in the neocortex", Nature Neuroscience 1(7):587-594 (1998).

Fukuda et al, "GABAergic Axon Terminals at Perisomatic and Dendritic Inhibitory Sites Show Different Immunoreactivities Against Two GAD Isoforms, GAD67 and GAD65, in the Mouse Hippocampus: A Digitized Quantitative Analysis", The Journal of Comparative Neurology 395:177-194 (1998).

Jovanovic et al, "Synapsins as mediators of BDNF-enhanced neurotransmitter release", Nature Neuroscience 3(4):323-329 (2000).

Miesenböck et al, "Visualizing secretion and synaptic transmission with pH-sensitive green fluorescent proteins", Nature 394:192-195 (1998).

Löscher, Wolgang, "Animal models of epilepsy for the development of antiepileptogenic and disease-modifying drugs. A comparison of the pharmacology of kindling and post-status epilepticus models of temporal lobe epilepsy", Epilepsy Research 50:105-123 (2002).

Stevens et al, "Identification of a Novel Process Limiting the Rate of Synaptic Vesicle Cycling at Hippocampal Synapses", Neuron 24:1017-1028 (1999).

Sankaranarayanan et al, "The Use of pHluorins for Optical Measurements of Presynaptic Activity" Biophysical Journal 79:2199-2208 (2000).

Takamori et al, "Identification of Differentiation-Associated Brain-Specific Phosphate Transporter as a Second Vesicular Glutamate Transporter (VGLUT2)", The Journal of Neuroscience 21:RC182 1 of-6 to 6 of 6 (2001).

Stevens et al, "'Kis and run" exocytosis at hippocampal synapses, 97(23):12828-12833 (2000).

Taupin et al, "Subcellular fractionation on Percoll gradient of mossy fiber synaptosomes: evoked release of glutamate, GABA, aspartate and glutamate decarboxylase activity in control and degranulated rat hippocampus", Brain Research 644:313-321 (1994).

Ryan et al, "The Kinetics of Synaptic Vesicle Recycling Measured at Single Presynaptic Boutons", Neuron 11:713-724 (1993).

Bellocchio et al, "The Localization of the Brain-Specific Inorganic Phosphate Transporter Suggests a Specific Presynaptic Role in Glutamatergic Transmission", The Journal of Neuroscience 18(21):8648-8659 (1998).

Dumoulin et al, "Presence of the vesicular inhibitory amino acid transporter in GABAergic and glycinergic synaptic terminal boutons", Journal of Cell Science 112:811-823 (1999).

Afzal et al, "Rapid Determination of Glutamate Using HPLC Technology", Methods in Molecular Biology 186:111-115 (2002).

Kupferberg, Harvey, "Animal Models Used in the Screening of Antiepileptic Drugs", Epilepsia 42(Suppl. 4):7-12 (2001).

* cited by examiner

*Primary Examiner*—Manjunath Rao
*Assistant Examiner*—Sandra Wegert
(74) *Attorney, Agent, or Firm*—Nixon & Vanderhye P.C.

(57) ABSTRACT

The present invention relates to a method of identifying agents suitable for use in treating epilepsy and other brain disorders, including but not limited to bipolar disorder, schizophrenia and depression. The invention further relates to methods of treatment based on the use of agents so identifiable.

11 Claims, 6 Drawing Sheets

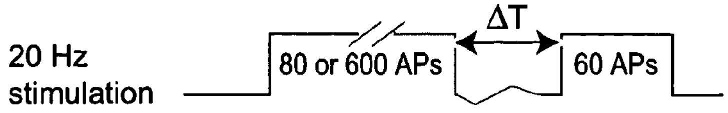
Fig. 3A
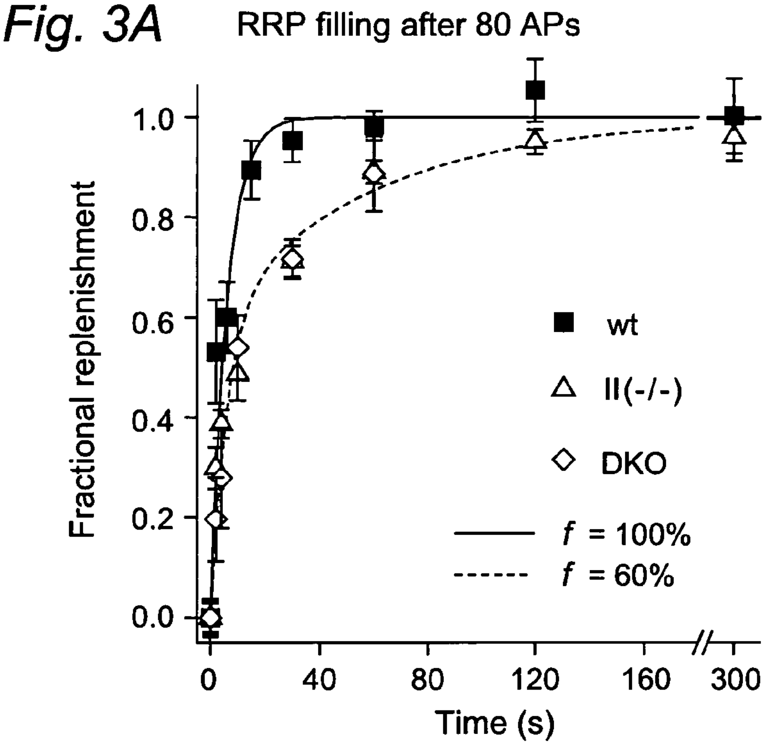
Fig. 3B
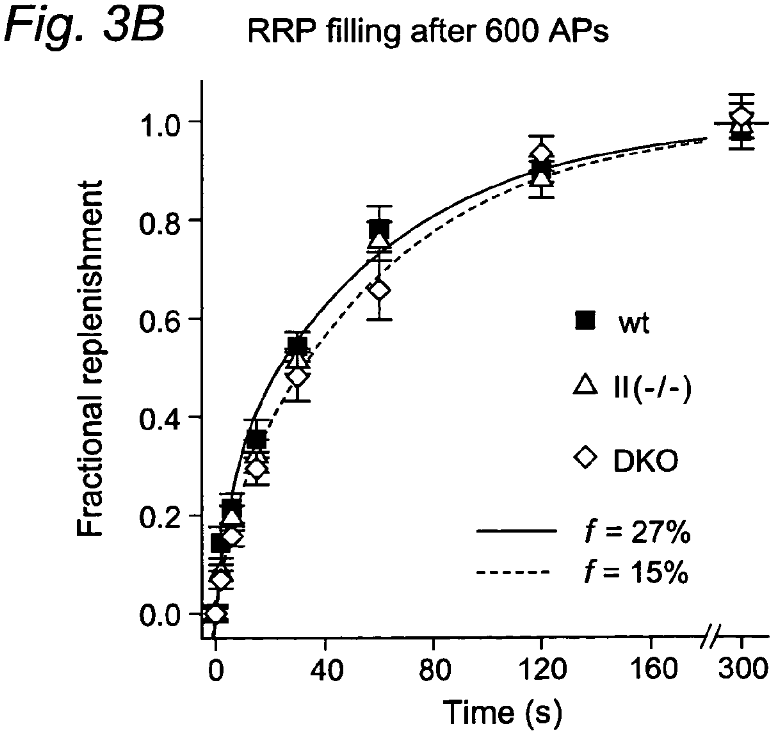

Fig. 6A
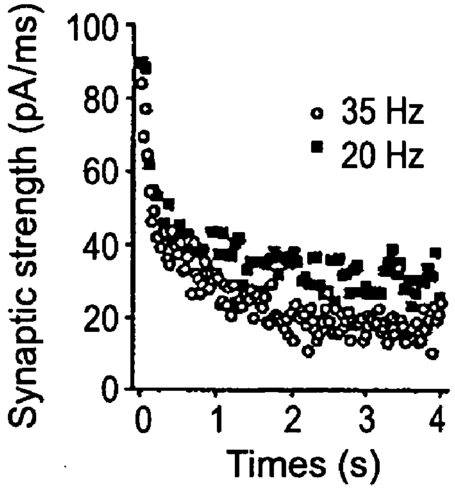
Fig. 6B
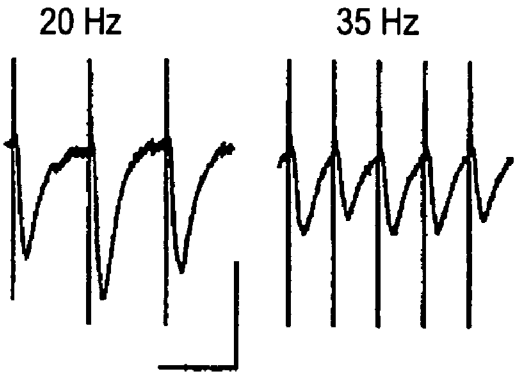
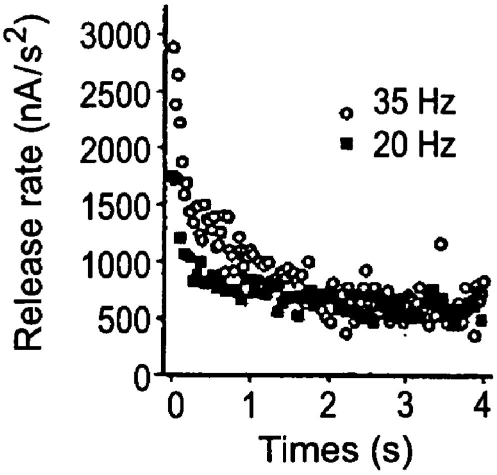
Fig. 6C
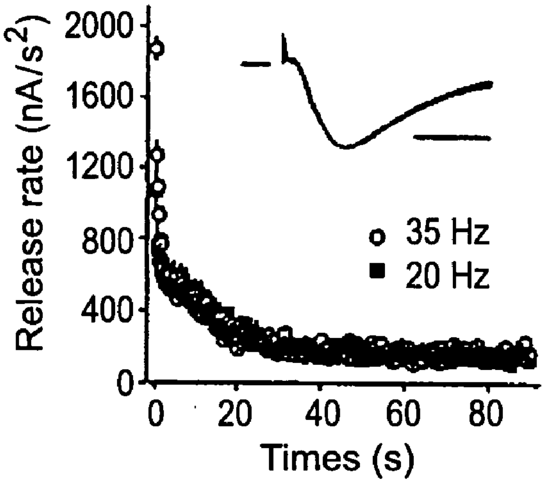
Fig. 6D

METHOD OF IDENTIFYING THERAPEUTIC AGENTS FOR THE TREATMENT OF EPILEPSY

This application claims priority from U.S. Provisional Application No. 60/433,972, filed Dec. 18, 2002, the entire content of which is incorporated herein by reference.

TECHNICAL FIELD

The present invention relates to a method of identifying agents suitable for use in treating epilepsy and other brain disorders, including but not limited to bipolar disorder, schizophrenia and depression. The invention further relates to methods of treatment based on the use of agents so identifiable.

BACKGROUND

Epilepsies comprise a diverse collection of disorders that affect an estimated 1-4% of the population in the United States. Epileptic seizures, which are generally self limiting, are the outward manifestation of excessive and/or hypersynchronous abnormal activity of neurons in the cerebral cortex. The behavioral features of a seizure reflect function of the portion of the cortex where the hyper activity is occurring. Generalized seizures, which appear to involve the entire brain simultaneously, can result in the loss of consciousness only and are then called absence seizures (previously referred to as “petit mal”). Alternatively, the generalized seizure may result in a convulsion with tonic-clonic contractions of the muscles (“grand mall” seizure). Some types of seizures, partial seizures, begin in one part of the brain and remain local. An individual suffering a partial seizure may remain conscious. If the individual loses consciousness, the seizure is referred to as a complex partial seizure. Current drug therapies operate either by regulating postsynaptic responses to neurotransmitter or by blocking presynaptic transmitter release machinery at a step prior to exocytosis (e.g., by inhibiting calcium and sodium channels). Such therapies can reduce seizure frequency in the majority of patients but it is estimated that only about forty percent are free of seizures despite optimal treatment. Unfortunately, currently available drug treatments are often associated with onerous side effects because—in addition to preventing seizures—they affect normal brain function as well.

Synapsins are the most abundant proteins associated with synaptic vesicles (De Camilli et al, Annu. Rev. Cell Biol. 6:433-60. (1990)). They are present in all of the most common types of presynaptic terminals: those that are activated primarily by action potentials (APs) (De Camilli et al, Annu. Rev. Cell Biol. 6:433-60 (1990)). Because they are extensively phosphorylated in an activity dependent fashion, and reversibly tether reserve vesicles to cytoskeletal elements within presynaptic terminals (Greengard et al, Science 259: 780 (1993)), they have long been thought to be involved in regulating the synaptic vesicle exo/endocytic cycle (De Camilli et al, Annu. Rev. Cell Biol. 6:433-60 (1990)). However, despite extensive molecular and physiological investigation, an identification of their role in neurotransmission has remained elusive—partly because techniques have only recently been developed that allow the individual rate-limiting steps in the vesicle cycle to be studied in isolation.

Several key experiments have implicated synapsins in the regulation of processes that afford synapses the ability to transmit signals during extended periods of heavy use. Synaptic strength temporarily weakens extensively during repetitive use, a phenomenon known as short-term depression (Zucker, Annu. Rev. Neurosci. 12:13-31 (1989)). Synapses with disrupted synapsin function (Pieribone et al, Nature 375:493-7 (1995), Hilfiker et al, Nat. Neurosci. 1:29-35 (1998), Humeau et al, J. Neurosci. 21:4195-206 (2001)), or synapses of mutant mice that lack synapsins (Rosahl et al, Cell 75:661-70 (1993), Rosahl et al, Nature 375:488-93 (1995), Li et al Proc. Nati. Acad. Sci. USA 92:9235-9 (1995), Terada et al, J. Cell Biol. 145:1039-48 (1999)), depress more quickly than do normal synapses, even though the basic cell biological machinery that underlies the exo/endocytic cycle seems to be intact (Rosahl et al, Cell 75: 661-70 (1993), Rosahl et al, Nature 375:488-93 (1995), Ryan et al, J. Cell Biol. 134:1219-27 (1996)). The precise kinetic role played by synapsins in short-term depression remains obscure.

Several of the kinetic components that underlie short-term depression by limiting the rate at which synaptic vesicles are prepared for release have been identified at excitatory synapses of the hippocampus (Stevens et al . Proc. Natl. Acad. Sci. USA 92:846 (1995), Stevens et al, Neuron 24:1017 (1999)). A typical synaptic terminal contains hundreds of vesicles laden with neurotransmitter but at any moment at most only a few percent of those are docked at the active zone, readily available to undergo exocytosis (Schikorski et al, J. Neurosci. 17:5858 (1997), Schikorski et al, Nat. Neurosci. 4:391 (2001)). These release-ready vesicles supply the transmitter used for intercellular signaling. During periods of heavy use, the readily releasable pool (RRP) of vesicles is quickly exhausted and the synaptic strength weakens because further transmission is only possible when new vesicles replace the spent ones within the pool.

The present invention is based, at least in part, on studies that have resulted in the elucidation of the biological mechanism responsible for synaptic fatigue. As a result of this understanding of mechanism, it has now been appreciated that agents that selectively reduce the size of the actively recycling vesicle pool at excitatory synapses can be used to prevent incipient seizures from developing into epilepsy. Such agents can be expected to avoid the onerous side effects inherent in currently available treatments as they should not affect synaptic function during periods of ordinary use.

SUMMARY OF THE INVENTION

The present invention relates generally to a method of identifying therapeutic agents. More specifically, the invention relates to a method of identifying agents suitable for use in treating epilepsy and other brain disorders, including but not limited to bipolar disorder, schizophrenia and depression. In addition, the invention relates to treatment methods based on the use of agents so identifiable.

Objects and advantages of the present invention will be clear from the description that follows.

BRIEF DESCRIPTION OF THE DRAWINGS

FIGS. 1A→1B (upper panels): During periods of heavy use, synapses quickly use up their RRPs (readily releasable vesicles are docked to release sites (green squares) in the active zone, and are released at a rate (green arrows) that is determined by the AP frequency). FIG. 1B. With the RRP empty, synaptic strength is limited by the rate at which fresh vesicles are prepared for release—a process that initially takes several seconds (blue arrows). FIG. 1C. After extensive use, some vesicles are prepared for release via a slow mode that takes minutes (rate constant of approximately 1/60s, denoted by pink arrows), slowing the overall rate of RRP replenishment and resulting in fatigue. This might be because of depletion of the reserve pool, or the interference of recycled vesicles that are not yet mature (pink). FIG. 1D. After 30 s of 20 Hz stimulation, only about ⅓ of the vesicles that are readied for release are prepared via the faster mode, and the synapse remains in a mostly fatigued steady state during continued use. Mutant synapses missing synapsin II (lower panels) fatigue more quickly than wt (compare syn II state (FIG. 1B) to wt state (FIG. 1C)), and also have smaller recycling pools that might deplete or be diluted by immature vesicles more quickly.

FIGS. 2A and 2B. Synaptic response sizes were normalized by the size of the first response in each train, and plotted versus the stimulus number. Blue squares are wt responses, red circles are DKO (mean of at least 7 trials, conducted on at least 4 preparations). Insets: blue traces represent wt responses, red is DKO. FIG. 2A. The first 160 responses. The mutant synapses depress more than wt, but a difference only emerges after the first 20 to 30 APs. Inset: averaged electrophysiological traces of the first responses. Scale bar is 100 pA vs 20 ms. FIG. 2B. All 900 responses, binned into groups of 10. Insets: i. Average of first 10 electrophysiological responses (scaled to match). ii. Identically scaled averages of responses number 150-159. Scale bar is 20 ms.

FIGS. 3A and 3B. RRPs of synapsin knockout synapses replenish more slowly than wt, but with the same stereotypical double exponential time course. RRP replenishment was monitored for wild type (wt), synapsin II knockout (syn II), and DKO synapses with pairs of 20 Hz trains separated in time by experimentally varied intervals as diagrammed at top. FIGS. 3A and 3B. RRP replenishment time course after 80 (FIG. 3A) or 600 (FIG. 3B) APs. Fractional replenishment for each interval was calculated as the sum of the 60 response sizes during the second stimulus train divided by the sum of the first 60 during the first train (after being corrected for the steady state response size as described in Stevens et al, Neuron 24:1017-28 (1999) and is plotted against the recovery interval (mean±SEM; at least 5 trials from 5 preparations for each). Solid squares represent wt recovery, open symbols represent mutants as indicated. All smooth curves represent Equation (1) with various values for f. FIG. 3A. Replenishment time course after 80 APs. The fraction of vesicles prepared for release via the faster mode (f in Equation (1))=60% for the mutant synapses, 100% for wt. FIG. 3B. Replenishment time course after 600 APs–f=15% for the mutant synapses, 27% for wt.

FIGS. 4A-4C. Synapses were activated with pairs of 20 Hz stimulus trains separated by fixed 20 s rest intervals as diagrammed above (FIG. 4A). FIG. 4A. The length of the first train of each pair was varied experimentally, and the amounts of RRP replenishment occurring during the 20 s rest intervals are plotted (left ordinate) against the cumulative sum of synaptic response sizes during the first train (mean±SEM for at least 6 trials from 3 preparations each—solid squares represent wt responses, open circles are DKO). The cumulative sum (abscissa) was first normalized by the sum of the first 30 response sizes, as this is approximately the response generated by the exocytosis of one RRP equivalent of transmitter. The contribution of the faster exponential component to the overall recovery time course (right ordinate) was also calculated—by back extrapolating the values on the left ordinate to t=0, assuming a single exponential with a 60 s time constant—which gives f in Equation (1). For a similar plot of wt data gathered with a different technique, see FIG. 6 of Stevens et al, Neuron 24:1017-28 (1999). The upper dashed line represents an arbitrary sigmoid fit to the wt data, and the lower one is identical except that its midpoint is shifted 40% to the left, and the entire curve is stretched vertically so that the steady state plateau is shifted 40% downwards. This provides a good fit for the DKO data. FIG. 4B. Values of f plotted in (FIG. 4A) are replotted (abscissa) versus the synaptic strength (ordinate) at the end of the first stimulus train of the corresponding pair. Relative synaptic strengths at the end of the first stimulus trains were all extracted from the first train of the longest pair (2000 APs). Normalized values for each trial were calculated as the average of the 60 responses occurring during continued stimulation that followed the number of stimuli in the corresponding first train, divided by the average response during the $4^{th}$ second of stimulation (e.g., normalized synaptic strength after 120 APs was calculated as the average response to stimuli 121-180 divided by the average elicited by stimuli 61-80). The gray box indicates data points representing trials where f was measured after stimulation trains that were too short to exhaust the RRP (<60 APs). Note that all other points fall about a straight line (mean±SEM; the solid line has a slope of 1.0). FIG. 4C. The amount of fatigue in the overall RRP replenishment rate was measured 20 s after 120 and 2000 APs for wt and several strains of mutants missing synapsin alleles as indicated. Fatigue (1−f) after 120 APs was quantified as the fraction of the maximum amount elicited by 2000 APs (mean±SEM for at least 10 experiments from 6 preparations each; significance was assessed with a students t test—p<0.05 (*, compared to wt), 0.01 (), 0.001 (*), 0.05 (#, compared to II(+/−), I(+/+)), 0.01 (##)). FIG. 4D. Blockade of the NMDA component of synaptic responses was monitored with low frequency stimulation in the presence of MK801 for wt and DKO synapses (n=6 for DKO, 5 for wt). Average response sizes are normalized by the size of the first response elicited in the presence of MK801 and plotted against the stimulus number.

FIG. 5A. Raw data examples of responses recorded when a synapse was fresh (upper trace) and after 50 s of repetitive activation (lower trace). Scale is 20 pA by 200 ms. The stimulus artifacts are blanked, the arrows indicate stimulus times. FIG. 5B. Probability of release vs. time during the first 3 s of stimulation (data are binned in groups of 3-14 trials, 4 preparations). FIG. 5C. Probability of release vs. time during the entire 90 s of stimulation (bins of 100; each data point is the average probability of release during a 5 s interval). The probability of release decreases dramatically during extended stimulation (FIG. 5B & 5C). FIG. 5D. Average amplitudes of successful responses (5s, 100 stimuli bins) vs. time (mean±SEM). Separate averages of the responses judged to be successes and failures are plotted in the inset. The large current inflections represent successes, the flat lines are failures. The traces in the left panel are the averages during the first 5 s of stimulation, on the right are the averages between 50 and 90 s. Scale is 10 pA by 20 ms. FIG. 5E. The cumulative number of quanta released during stimulation vs. time. Note that the terminals released only an average of 123 quanta over 90 s of continuous stimulation.

FIGS. 6A-6D. 20 Hz is fast enough to drive exocytosis at the maximal steady state rate. Schaffer collaterals were stimulated at 20 or 35 Hz for 90 s, while postsynaptic responses were recorded from a patch clamped pyramidal neuron. Open circles represent responses generated at 35 Hz, filled squares at 20 Hz in FIGS. 6A, 6C, and 6D. FIG. 6A. Synaptic strength during the first 4 s of stimulation. FIG. 6B. Responses after 2.5 s of stimulation (left panel is at 20 Hz, right at 35 Hz, scale bars are 100 pA by 50 ms). FIG. 6C. Data from (FIG. 6A) were multiplied by the corresponding stimulus frequency and replotted to show that the rate of release reached a similar level at both frequencies after the first several seconds of stimulation. FIG. 6D. Responses (calculated as in (FIG. 6C) for the entire stimulation) were binned (ten responses per bin), and plotted against the time of stimulation (mean±SEM; 5 trials each). After several seconds, release rates at both 20 Hz and 35 Hz plateau briefly at the same level and then decay with similar time courses before achieving the same low steady state rate. Inset: Overlay of 4 scaled traces of responses recorded at various times during 20 and 35 Hz stimulation (stimulus artifacts are blanked, scale bar is 10 ms). Individual traces represent the average of the first 10 individual responses at 20 Hz and at 35 Hz, and the averages of the last 100 responses at both frequencies. Since the individual responses evoked at 35 Hz do not decay away completely in the 29 ms interstimulus interval, the corresponding tail of the average 20 Hz response was first scaled to match the prestimulus-artifact baseline, and then subtracted from the average 35 Hz response. The shape of the EPSC (excitatory post synaptic current) was the same at both stimulus frequencies, and did not change during experiments even while the synaptic strength depressed to 5% of initial (during 35 Hz stimulation).

DETAILED DESCRIPTION OF THE INVENTION

Figures 1A, 1B, 1C, 1D:
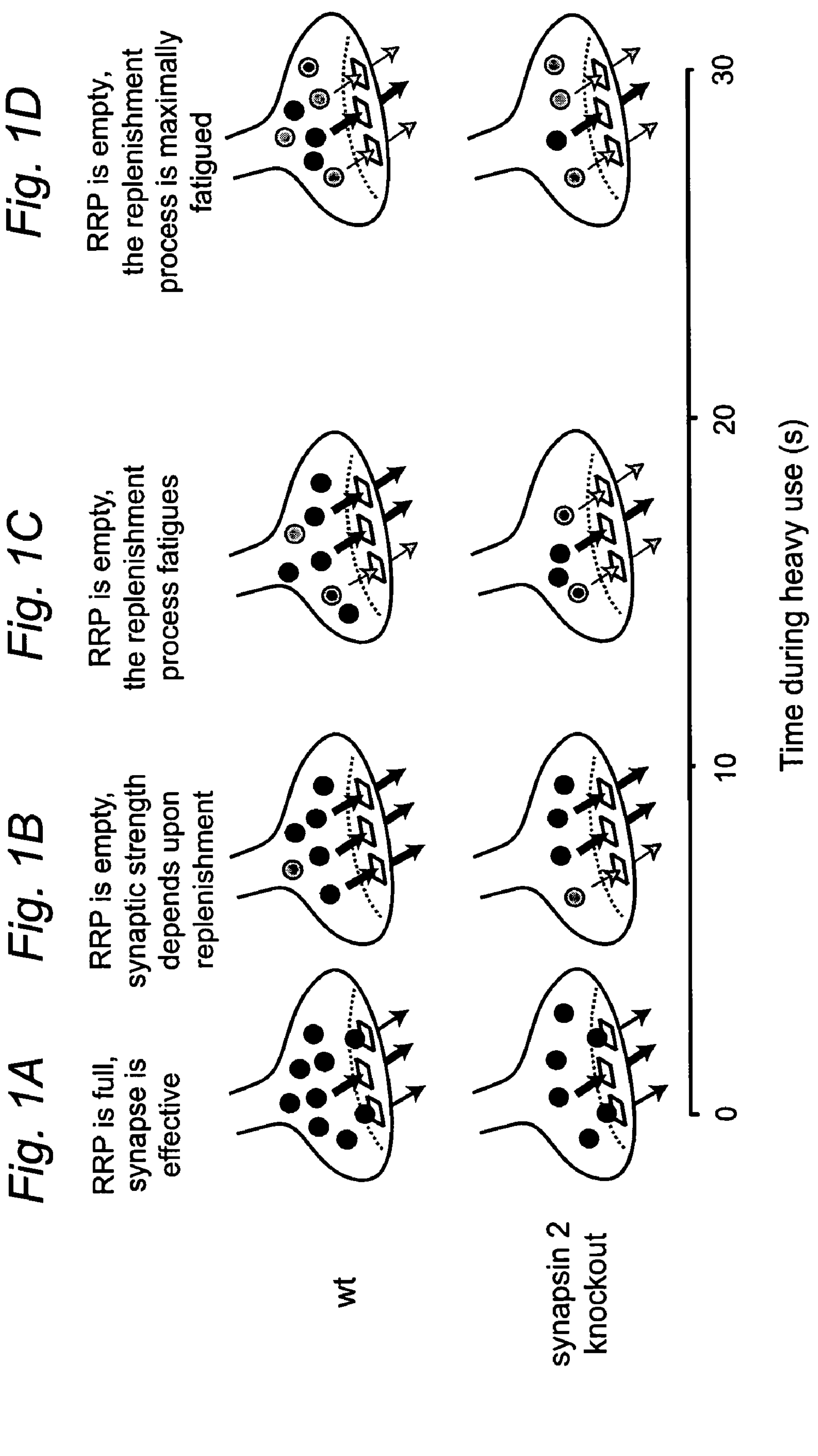
FIGS. 1A-1D. Working model of fatigue in the synaptic vesicle supply rate.

The present invention relates to a method of identifying agents that can be used to regulate the number of synaptic vesicles that are functionally available to participate in synaptic transmission during episodes of repetitive synaptic use lasting several minutes (these vesicles hereinafter being referred to as constituting the functional/recycling pool) and to agents so identified as being useful in the treatment of brain disorders such as, for example, epileptic seizures.

Synaptic transmission occurs when synaptic vesicles (small, subcellular, membrane delineated structures in the presynaptic terminal that store neurotransmitter) undergo exocytosis by fusing with the plasma membrane of the presynaptic terminal and thereby release neurotransmitter into the synaptic cleft. The liberated transmitter binds to receptors on the dendrites of the postsynaptic neuron, causing an electrical signal to be transduced. Most presynaptic terminals have hundreds of synaptic vesicles within them but, in excitatory terminals, only a few dozen routinely participate in synaptic transmission—these constitute the functional/recycling pool. Following exocytosis, spent synaptic vesicles are recycled (i.e., repackaged and refilled), this mechanism serves to replenish the functional/recycling pool.

The present invention is based, at least in part, on the realization that a form of short-term synaptic depression, referred to hereinafter as synaptic fatigue, or as fatigue, persists for several minutes after the functional/recycling pool has been exhausted. The functional/recycling pool becomes depleted during periods of heavy use because the bulk rate of vesicle recyclization is slower than the rate of vesicle use during such periods. The resulting synaptic fatigue is thus manifest as an effective attenuation of the efficacy of excitatory synapses during excessive use, such as during an epileptic seizure. This attenuation blocks the recurrent neuronal network excitation that is otherwise in part responsible for seizure propagation and expansion. Synaptic fatigue thus functions as a natural anti-seizure mechanism.

The present invention is also based in part on the realization that the onset of synaptic fatigue is super-linear with synaptic use (see FIG. 4.). Since the axons of excitatory synapses normally almost never fire long-lasting, high frequency trains of action potentials, fatigue ordinarily plays no role in synaptic function. However, when excitatory synapses are used extensively—as they are during the incipient stages of an epileptic seizure—some threshold level of functional/reserve pool exhaustion is reached and the synapses fatigue extensively, attenuating their efficacy, and limiting the spread of epileptic activity. The present invention relates to agents that reduce the standing size of the functional/recycling pool of synaptic vesicles at excitatory synapses, effectively making them exhaust more quickly during abnormal activity, thus resulting in the faster onset of synaptic fatigue (i.e., agents capable of shifting the wild type curve shown in FIG. 4A to the left). Such agents can be used in treating seizures by increasing the sensitivity for induction of this already functioning natural anti-seizure mechanism. Agents of the invention can be expected to avoid side effects inherent in currently available treatments because synaptic function during periods of ordinary activity should not be affected by their use.

In one aspect, the present invention relates to a method of screening test compounds for their ability to modulate (e.g., reduce) the size of the functional/recycling pool of vesicles. The number of vesicles in the functional/recycling pool can be measured, for example, with well developed optical and biochemical techniques, making it possible to screen large numbers of reagents quickly. For example, synapses can be probed in vitro in the presence and absence of test compound and the relative number of functionally recycling vesicles determined. The determination of relative vesicle number can be made, for example, using fluorescent monitoring or standard synaptosomal assays.

Fluorescent monitoring of the size of the functional/recycling pool in synapses grown in cell culture can be effected, for example, by transfecting neurons with genetically encoded variants of green fluorescent proteins (GFP) that are targeted to synaptic vesicles and that only fluoresce when vesicles undergo exocytosis (synapto-pHluorins) (Miesenbock et al, Nature 394(6689):192-5 (1998)). A similar result can be achieved by harvesting neurons for cell culture from animal strains that have been transgenically altered to express synapto-pHluorins. Alternatively, recycling vesicles can be labeled with externally applied lipophilic dyes (such as FM1-43, and a family of derivatives with altered lipophilic and optical properties) during periods of activity (Ryan et al, Neuron 11(4):713-24 (1993)). The first of these techniques measures exocytosis, the second endocytosis. In either case, fluorescence can be detected, for example, with standard (Stevens and Williams, Proc. Natl. Acad. Sci. USA 97(23): 12828-33 (2000)), confocal (Ryan et al, Neuron 11(4):713-24 (1993)), Sankaranarayanan et al., Biophys. J. 79(4):2199-208) (2000)), or 2-Photon fluorescence microscopic techniques. The functional/recycling pool size can be measured as the total amount of exo/endocytosis that occurs during several minutes of stimulation at the maximum rate (e.g., about 10 Hz or above), or with the application of standard salts for a similar period.

In the standard synaptosomal assay approach to determining the number of vesicles constituting the functional/reserve pool, purified preparations of synaptic terminals can be used (Sihra, T. S. in *Posttranslational Modifications: Techniques and Protocols* (ed. Hemmings, H. C. Jr.) 67-119 (Humana Press, Totowa, N.J., 1997)). In accordance with this assay, the size of the recycling pool is determined by measuring the amount of neurotransmitter that is released upon depolarization (accomplished with the addition of standard salts). A test compound that alters the size of the functional/recycling pool will alter the amount of neurotransmitter released (the primary excitatory neurotransmitter in the brain is glutamate which can be detected, for example, using HPLC (Taupin et al, Brain Res; 644(2):313-21 (1994)), Afzal et al, Methods Mol. Biol. 2002:186:111-115 (2002)). Glutamate released from synaptosomes can also be monitored in real time, for example, fluorescently as NADP is transformed to NADPH via exogenously added glutamic acid decarboxylase by standard spectrophotometry methods (e.g., Jovanovic et al, Nat. Neurosci. 3(4):323-9 (2000)). Using similar approaches, the determination can also be made as to whether a test compound alters the number of functional/recycling vesicles in inhibitory, GABA-ergic nerve terminals (GABA=4-aminobutyrate (Taupin et al, Brain Res. 644(2):313-21 (1994)).

In a second aspect, the present invention relates to a method of determining which of the test compounds found capable of reducing the size of the functional/recycling pool at excitatory synapses do not similarly affect inhibitory synapses. Although the axons of the majority of neurons in primary cell cultures make excitatory synaptic connections, the cultures also contain a minority of neurons that make inhibitory synapses (Bekkers et al, Proc. Natl. Acad. Sci. USA 88(17): 7834-8 (1991)). The functional/recycling pool can be monitored fluorescently at inhibitory synapses in the same way as at excitatory synapses.

Synapse type can be distinguished in several ways. For example, after determination of the functional/reserve pool size, standard immunohistochemical techniques can be used to stain synapses for proteins unique to inhibitory synapses (using, for example, antibodies raised against glutamic acid decarboxylase (Fukuda et al, J. Comp. Neurol. 395(2):177-94 (1998)) or unique to excitatory synapses (using, for example, antibodies raised against a vesicular glutamate transporter (Takamori et al, J. Neurosci. 21(22):RC182 (2001)). Identification of synapse type can also be performed in real time with fluorescent techniques, thereby avoiding the immunohistochemical step. Recently, transgenic mice have been generated that express GFP only in the fast-spiking inhibitory interneurons (Bartos et al, Proc. Natl. Acad. Sci. USA 99:13222-13227 (2002)). Neurons harvested from this strain of mice, or from others where a fluorescent marker is expressed differentially in inhibitory or excitatory neurons, can be grown in culture on isolated substrate "islands" (Bekkers et al., Proc. Natl. Acad. Sci. USA 88(17):7834-8 (1991)) allowing the efficient identification of synapse type (inhibitory versus excitatory). Overlapping fluorescence spectra due to the simultaneous use of two types of indicators (one to identify the neuron type, one to determine the effects of agents on the functional/recycling pool size) will not confound the basic assay as there are genetically encodable fluorescent proteins, as well as lipophilic fluorescent dyes in the FM1-43 family, of several colors. The requirement for growing neurons in isolation can be avoided by harvesting neurons from mouse strains expressing synapto-pHluorins or similar markers of vesicle turnover differentially in inhibitory versus excitatory synapses.

Once candidate therapeutic agents are identified using, for example, methods described above, such candidate agents can be screened for effectiveness in modulating the onset of synaptic fatigue using, for example, electrophysiological techniques in brain slices, such as those. used to generate FIG. 4 (see also Galaretta and Hestrin, Nat. Neurosci. 1(7):587-94 (1998)), or in cell culture as described by Stevens and Wesseling (Neuron 24(4):1017-28 (1999)).

Agents that modulate the size of the functional/recycling pool, and thereby the onset synaptic fatigue during heavy synaptic use, can then be tested in animals. Several animal models are available for confirming effectiveness at seizure prevention (Kupferberg, Epilepsia. 42 Suppl 4:7-12 (2001)); Loscher, Epilepsy Res. 50(1-2):105-23 (2002)).

The invention relates to the screening methods described above and to agents so identifiable. Agents of the invention can be formulated using standard techniques so as to yield compositions suitable for administration to mammals (human and non-human (e.g., dogs and cats)) in need thereof. The compositions can include, for example, a pharmaceutically acceptable carrier, excipient or diluent. The choice of the carrier, excipient, diluent, or the like, can be selected based on whether the resulting composition is to be administered, for example, orally, intravenously, intraperitoneally, intradermally, intramuscularly, intranasally, buccally or topically. For oral administration, compositions can be present in dosage unit form, e.g., as tablets, pills, capsules, granules, drops, or the like, while for parenteral administration, the composition can take the form, for example, of a solution or suspension (advantageously sterile). Compositions suitable for topical administration can be present as, for example, liquids, creams gels or ointments. Compositions suitable for inhalative administration can be present in forms suitable for use as sprays. Agents of the invention can also be formulated as depot formulations, e.g., in dissolved form or in a transdermal device, optionally with the addition of agents promoting penetration of the skin when percutaneous administration is contemplated. Orally or percutaneously usable forms can provide for the delayed release of the agents of the invention. The amount of agent administered will depend, for example, on the nature of the agent, the status of the patient and the effect sought. Establishment of optimum dosing regimens is well within the skill level of one in the art.

Since at least certain of the pharmaceuticals that are currently available to treat epilepsy also are effective in treating brain disorders such as schizophrenia, bipolar disorder, depression, mood disorders, dysthemia, headache, trigeminal neuralga, neuropathic pain, anxiety and sleep disorders, the present invention also encompasses the use of agents identifiable using the screening methods described herein in the treatment of such disorders. Agents identifiable using the present screens can also be used for sedation.

Certain aspects of the invention can be described in greater detail in the non-limiting Example that follows.

EXAMPLE I

Experimental Details:

Colonies of synapsin I and synapsin II knockout mice were obtained from Jackson Labs and were crossed to obtain double knockout and heterozygous strains. Mice were genotyped by PCR analysis using oligonucleotide primers designed to recognize mutant and wt alleles as reported previously (Rosahl et al, Cell 75:661-70 (1993), Rosahl et al, Nature 375:488-93 (1995)).

Electrophysiological experiments were performed on 400 μm thick hippocampal slices of two to three week old mice. Briefly: the extracellular recording solution contained (in mM) 120 NaCl, 1.25 $NaH_2PO_4$, 26 $NaHCO_3$, 10 glucose, 3.5 KCl, 2.6 $CaCl_2$, 1.3 $MgCl_2$, picrotoxin (50 μM), and usually APV (50 μM—except for the MK801 experiments when 5 μM DNQX was included instead), and was bubbled continuously with a mixture of 95% $O_2$ and 5% $CO_2$. Whole cell patch clamp recordings were performed using three to five megaohm pipettes, filled with (in mM) 130 Cs-gluconate, 5 CsCl, 5 NaCl, 2 $MgCl_2$, 2 MgATP, 0.2 LiGTP, 1 EGTA, 0.2 $CaCl_2$, and 10 HEPES. Synaptic responses were evoked with a monopolar silver/silver chloride stimulating electrode inserted into a glass pipette filled with recording solution (tip diameter between 20 and 40 μm) and placed in the Schaffer collaterals. Synaptic strength was measured as the current integrals of the resulting electrophysiological responses. Synapses were always given at least 4 minutes of rest before each experiment was initiated. Data were only accepted if the access resistance did not change throughout individual trials.

For some experiments, MK801 was included as indicated. For these, NMDA currents (recorded at −20 mV) were first monitored at low frequency (⅛ Hz) in the absence of NMDA receptor blockers. Following 10 minutes of rest during MK801 application, currents were again monitored as before.

Results:

These studies result in the identification of the specific kinetic element in the synaptic vesicle cycle that is regulated by synapsin II, and that underlies a component of short-term depression at Schaffer collateral synaptic terminals. Two kinetic elements of the cycle have been identified recently that limit the rate at which vesicles are prepared for release to support synaptic transmission during periods of heavy use at these excitatory hippocampal synapses (Stevens et al, Proc. Natl. Acad. Sci. USA 92:846-9 (1995), Rosenmund et al, Neuron 16:1197-207 (1996), Stevens et al, Neuron 24:1017-28 (1999), Pyle et al, Neuron. 28:221-31 (2000)) (see FIG. 1). During the first several seconds of use, reserve synaptic vesicles are supplied by a process that takes several seconds. During more extended episodes, a second rate-limiting process emerges; many of the vesicles that become available for release only do so via a much slower mode that takes minutes (Stevens et al, Neuron 24:1017-28 (1999), Pyle et al, Neuron. 28:221-31 (2000)). As the number of vesicles that are prepared for release by the faster mode declines and the fraction prepared via the slower mode correspondingly increases, the overall rate at which vesicles are supplied for exocytosis slows down—a phenomenon referred to here as fatigue. Mutant synapses missing synapsin II fatigue more quickly than their wt counterparts because the slower mode of vesicle trafficking begins to dominate earlier in mutant terminals than it does in their wt counterparts during extensive periods of heavy use.

Figure 2B:
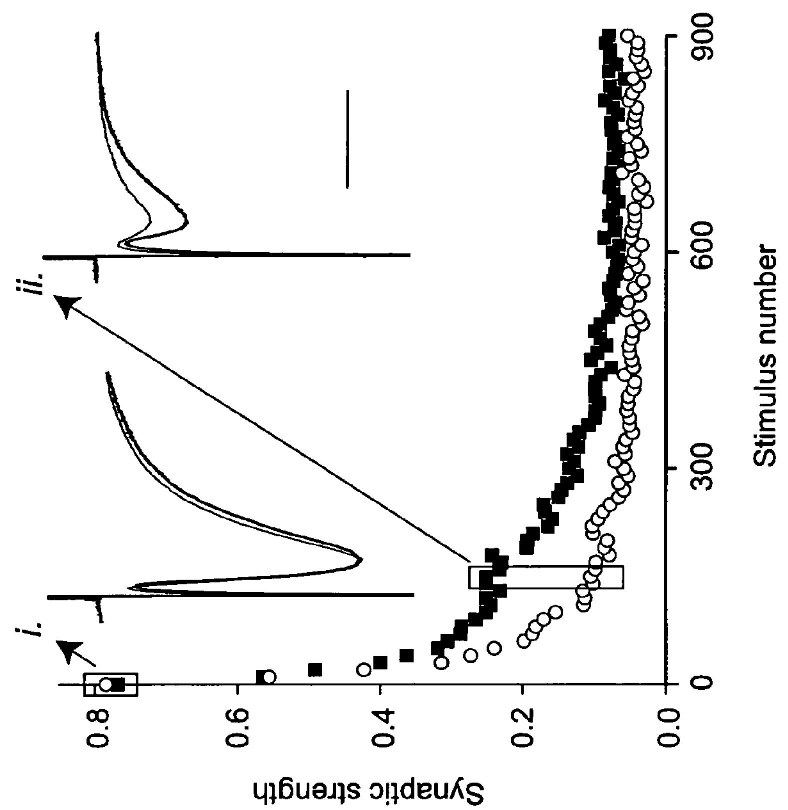
FIGS. 2A and 2B. Synapses missing synapsins I and II (DKO) depress sooner and more extensively during heavy use. Schaffer collaterals were stimulated at least 900 times at 20 Hz while postsynaptic responses were recorded from patch, clamped CA1 pyramidal neurons in slices taken from age matched wt and DKO animals.
Figure 2A:
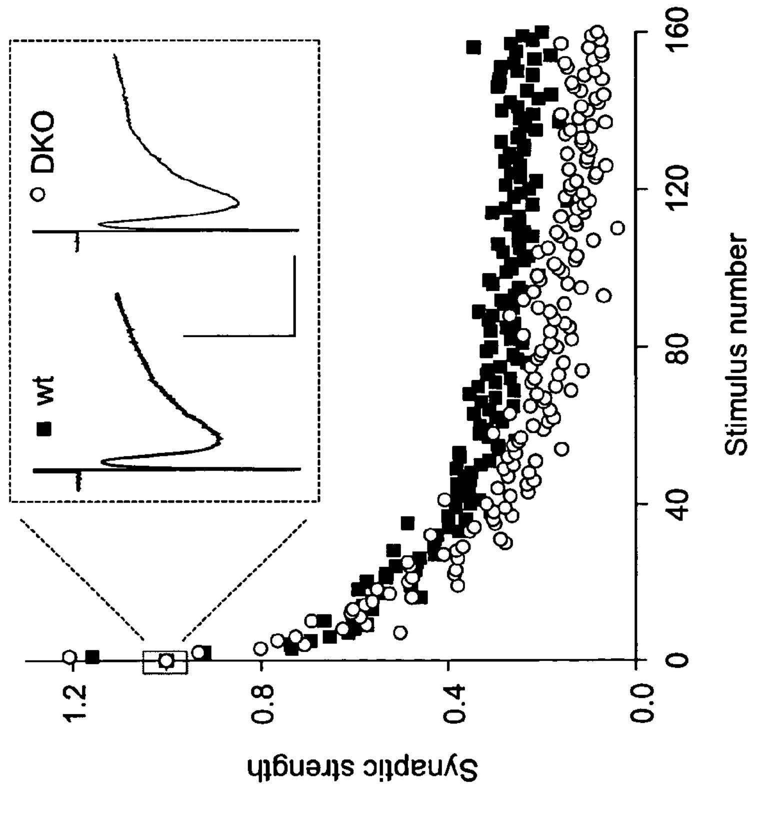

Synapses missing synapsins I and II exhibit more short-term depression: FIGS. 2A and 2B confirm that synapses of mice missing the genes encoding synapsin I and II (DKO) exhibit more short-term depression than their wild type (wt) counterparts during high frequency use (Rosahl et al, Nature 375:488-93 (1995)). Both wt and DKO synaptic responses recorded from patch clamped CA1 pyramidal neurons depressed substantially during extensive presynaptic Schaffer collateral stimulation (900 stimuli at 20 Hz) in slices from age matched mice. There was no difference in the amount of depression evident in the responses to the first several dozen stimuli, but thereafter the DKO synapses depressed more than wt (FIG. 2A). After about 600 stimuli, the strengths of both sets of synapses reached low steady state levels that did not diminish further for the next 15 s of continuous stimulation (FIG. 2B). This steady state synaptic strength was weaker at mutant terminals than at wt controls with wt synapses depressing to 7.3% of their initial strength, while DKO synapses depressed to 4.2%.

RRP replenishment rate is slower in mutant synapses after moderate amounts of use: Most of the extra depression exhibited by the mutant synapses occurred after the initial pool of readily releasable vesicles had been exhausted. Typical synaptic terminals contain hundreds of vesicles laden with neurotransmitter but at any moment at most only a few percent of these are docked at the active zone, readily available to undergo exocytosis quickly: these vesicles are collectively referred to as the readily releasable pool (RRP) (Schikorski and Stevens, Nat. Neurosci. 4:391-5 (2001)). After these vesicles have been expended—as they are during the first several seconds of 20 Hz stimulation—the rate at which they are replaced plays a major role in determining the synaptic strength. The time course of the more severe short-term depression in mutant terminals thus suggested that they have a defect in one of the kinetic processes that control the overall rate at which synaptic vesicles are supplied to replenish the RRP.

To determine if the kinetic defect is related to the overall rate at which vesicles are supplied for release, the time course of RRP replenishment was monitored both for mutant (synapsin II knockout (syn II) and DKO) and wt synapses after being depressed by either moderate (80 APs—FIG. 3A), or longer-lasting (600 APs—FIG. 3B) stimulus trains (20 Hz). Each stimulus train used to induce depression was followed by an experimentally varied rest period for RRP replenishment, and then another test train that was long enough to dump the contents of the RRP again (at least 60 APs), as diagrammed at the top of FIG. 3. An estimate of the amount of RRP replenishment during each inter-train interval was obtained by dividing the sum of the first 60 responses during the second train of each pair by the sum of the first 60 responses evoked during the first train as described previously (Stevens et al, Neuron 24:1017-28 (1999)).

It took substantially longer for the RRPs of mutant terminals to be replenished after the moderate (80 APs) stimulation when compared to wt (FIG. 3A). Replenishment after more extensive use (600 APs) was slower for both mutant and wt synapses than it was for the mutants after moderate stimulation (compare FIG. 3A and FIG. 3B). And, although the difference was less dramatic than after 80 APs, the mutant synapses recovered even more slowly than wt after the longer stimulus train (FIG. 3B). These results indicate that the overall RRP replenishment rate in mutant terminals is indeed slower than in their wt counterparts, at least under some conditions. The defect seems to be predominantly due to the absence of synapsin II as the RRPs of synapsin II null terminals recovered just as slowly as those also missing synapsin I (i.e. DKO).

The overall RRP replenishment rate would be slower if a larger fraction of the vesicles supplied for release were prepared via the slower trafficking mode, or if the kinetics of either of the modes were themselves slowed (see FIG. 1). Strikingly, a kinetic analysis showed that neither the faster nor the slower mode by which vesicles normally replenish the RRP is altered in the mutant terminals, indicating that a larger fraction of the vesicles supplied for release were prepared via the slower mode in the mutants.

All recovery time courses after moderate and extensive amounts of stimulation, for both mutant and wt synapses, proceeded with the same stereotypical double exponential function with fixed time constants (see the theoretical curves in FIGS. 3A and 3B)—as demonstrated previously for wt synapses (Stevens et al, Neuron 24:1017-28 (1999)). That is, the recovery time courses were fit by:

$$s(t) = f \cdot \left(1 - e^{\frac{-t}{\tau_f}}\right) + (1 - f) \cdot \left(1 - e^{\frac{-t}{\tau_s}}\right) \tag{1}$$

where s(t) is the fraction of the RRP that has replenished after a rest interval of time t, $\tau_f$=6s, $\tau_s$=60s . (This equation is formally identical to Equation (1) in Stevens et al, Neuron 24:1017-28 (1999)—see this reference for wt recovery time courses after intermediate amounts of stimulation). As the two component exponentials that make up Equation (1) describe the time courses over which vesicles are prepared for release via the two vesicular trafficking modes (Stevens et al, Neuron 24:1017-28 (1999)), the observation that the time constants (6 s and 60 s) are the same in mutant and wt synapses indicates that the kinetics of the two modes themselves are not affected by the presence or absence of synapsins I and II.

The only variable in Equation (1) that was affected by synapsin II deletion was f, which is the relative weighting of the faster component exponential. This parameter represents the fraction of the vesicles that replenish the RRP via the faster mode, while (1−f) is the remaining fraction of vesicles that are prepared for release via the slower mode. After 80 APs, the entire RRPs in the wt terminals were replenished with vesicles prepared via the faster mode (FIG. 3A, f=100%), while only 60% of the mutant RRPs were replenished quickly, leaving 40% to be replenished via the slower mode. After the 600 AP train, 27% of the wt RRPs were replenished via the faster mode, compared to only 15% for the mutants (FIG. 3B). The RRPs of the mutant terminals thus replenished more slowly than their wt counterparts because the slower mode of vesicular maturation played a larger role in the replenishment process at the mutant terminals in these experiments.

Mutant terminals fatigue more quickly than wt.: Does the overall rate of RRP replenishment fatigue more quickly during heavy use, or is replenishment always slower in mutant terminals? To compare how the relative contributions of the two modes of vesicular trafficking change with synaptic use for mutant and wt synapses, the fraction of the overall RRP replenishment process that is governed by the faster mode was measured after a series of 20 Hz trains of various lengths in a set of experiments similar to the ones documented in FIG. 3—in this case with a fixed time interval of 20 s. Initially, the overall RRP replenishment rate was just as fast at mutant terminals compared to wt; after the shortest stimulus trains (20 APs), all of the vesicles that were readied for release were supplied via the faster mode at both wt and DKO synapses. After all other stimulus trains (60 or more APs), however, a smaller fraction of the vesicles were prepared for release via the faster mode in mutant terminals. This indicates that the complementary, slower mode of vesicular trafficking (1−f) emerged to play a substantial role sooner in mutant than in wt synapses, and that the overall RRP replenishment rate thereby fatigued earlier in mutant terminals during extended periods of stimulation.

Figure 4B:
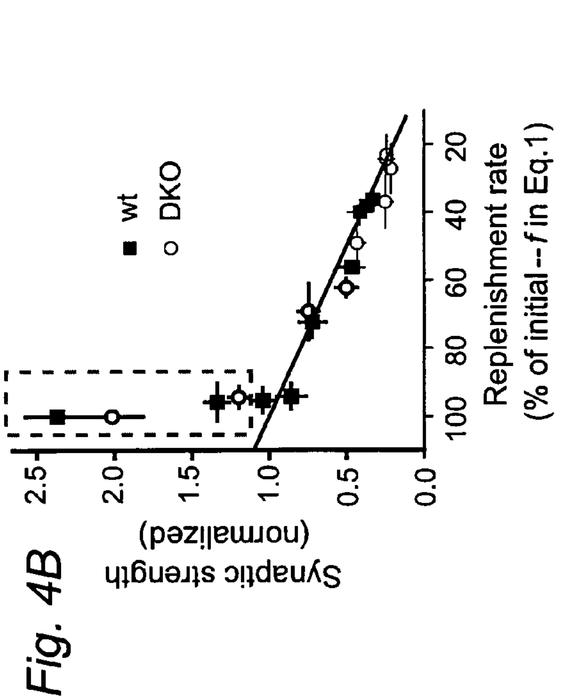
FIGS. 4A-4D. Synapses missing synapsins I and II fatigue more quickly than wt.
Figure 4D:
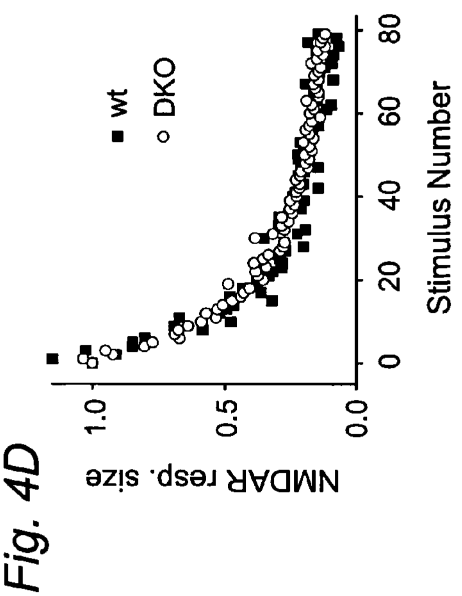
Figure 4A:
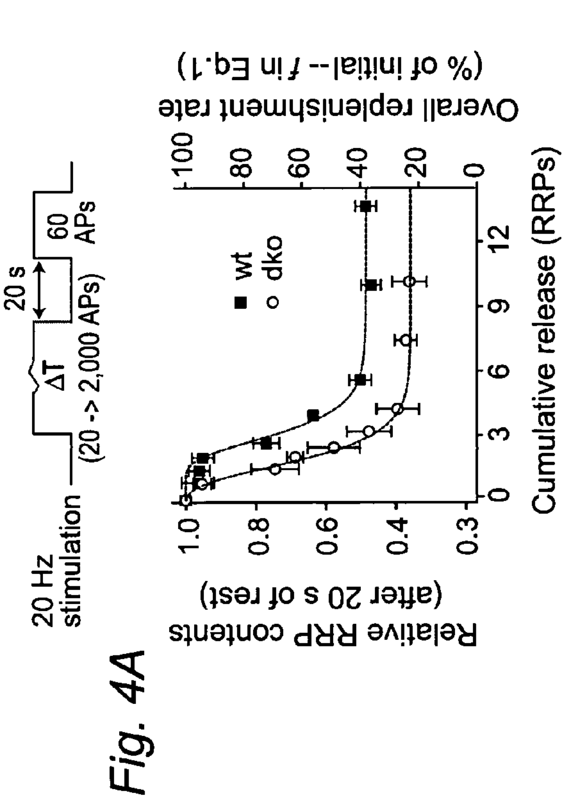
Figure 4C:
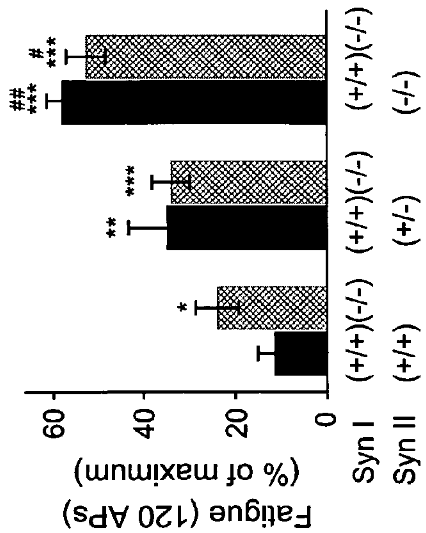

The fraction of releasable vesicles that were readied via the faster trafficking mode is plotted against the cumulative amount of transmitter release elicited during the first stimulus train of each pair in FIG. 4*a* because the amount of fatigue in the overall RRP replenishment rate depends upon the cumulative amount of exocytosis—and not strictly upon other measures of activity such as the number of APS (Stevens et al, Neuron 24:1017-28 (1999)). FIG. 4A shows that while the overall RRP replenishment rate does not begin to slow down at wt synapses until after several RRP equivalents of synaptic vesicles have undergone exocytosis, the overall rate does begin to fatigue soon after the first round of exocytosis at DKO synapses.

FIG. 4B shows that the fraction of vesicles readied for release via the faster mode (f) was proportional to the synaptic strength for all but the first 60 responses during 20 Hz stimulation for both mutant and wt synapses (data points fit by the straight line in FIG. 4B). This result was anticipated because the first 60 APs are enough to empty the initial RRP, and thereafter, synaptic strength is determined by the amount that the RRP replenishes during the brief intervals between stimuli—an amount that is set by the overall rate of RRP replenishment. Fatigue in the overall RRP replenishment rate is thus the primary cause of the component of short-term depression that accumulates after the first 60 APs, although other factors—such as the progressive depletion of the RRP—contribute to the depression that appears during the first 60 stimuli (data points within the gray box in FIG. 4B). The mutant terminals thus depress faster than the wt ones because the RRP replenishment process fatigues more quickly, and the terminals are not capable of maintaining transmission at the same level for as long as their wt counterparts.

Allele-dosage dependence of fatigue onset: To determine a possible dosage dependence of fatigue onset on the number of missing synapsin I and II alleles, the amount of fatigue in the overall RRP replenishment rate was measured for synapses of animals missing either one or both synapsin II alleles, in both wt and synapsin I null backgrounds. The time course of RRP replenishment was determined after trains of 120, and 2000 stimuli (20 Hz) for the expanded data sets as above. The fraction of the release-ready vesicles prepared via the slower trafficking mode (1−f) following the shorter trains is plotted in FIG. 4C relative to the maximum value obtained after the longer stimulus trains consisting of 2000 stimuli. The results show that the onset of fatigue depends strongly upon the number of missing synapsin II alleles but only modestly upon the presence or absence of synapsin I. The effect of knocking out synapsin I on this parameter is apparently masked when even a single allele of synapsin II is missing.

Synapsin II is involved in regulating a kinetic element of the exo/endocytic cycle: The more rapid onset of fatigue in the overall rate at which vesicles are supplied for release strongly suggests that synapsin II is directly involved in regulating the RRP replenishment process but an alternate possible explanation is that the difference could instead be the indirect result of a heretofore hidden enhancement of the release machinery in the mutants. That is, since fatigue results from the use of transmitter stores (Stevens et al, Neuron 24:1017-28 (1999)), synapses that initially release more transmitter might also be expected to exhibit fatigue more quickly. Arguing against this alternative, however, is the observation that synaptic strength depresses more quickly at mutant compared to wt synapses (FIG. 2); a result that suggests that less transmitter is released by mutant terminals than by wt ones during comparable periods of use. However, since the measures of synaptic strength reported here have been normalized by the sizes of the first responses during each stimulation, this logic is only valid if the initial probability of release is the same—or less—at mutant synapses compared to wt.

To test this, the time course of MK801 blockade of synaptic responses carried by the NMDA subtype of glutamate receptors was measured during low frequency stimulation at both DKO and wt synapses (Rosenmund et al, Science 262:754-7 (1993), Hessler et al, Nature 366:569-72 (1993), Huang et al, J. Neurophysiol. 78:2870-80 (1997)). There was no difference in the time course of blockade between mutants and wt (FIG. 4D), indicating that the initial probability of release is unaltered in mutant terminals (Manabe et al, Science 265: 1888-92 (1994)). Taken together with the observation that the mutant synapses depress more quickly than their wt counterparts when used heavily (FIG. 2), these results indicate that the mutants cumulatively release less transmitter than wt during comparable amounts of use. The more rapid onset of fatigue in the mutants thus must directly reflect an alteration in the process that normally controls how many vesicles can be prepared for release via the faster of the two trafficking modes, before the slower mode begins to dominate during extended periods of heavy use.

Summarizing, these studies identify the kinetic difference between the synapses of mice with and without synapsin II that causes the mutants to depress more quickly when used heavily. When both types of synapses are fresh, it takes several seconds for synaptic vesicles to be readied to undergo exocytosis to support intercellular communication. However, during extensive episodes of intense activity, presynaptic terminals become fatigued, and many vesicles are prepared for release via a much slower mode that takes minutes. Mutant terminals missing synapsin II fatigue substantially more quickly and eventually more extensively than their wt counterparts (FIG. 1B). The effect is specific for the onset of fatigue in the overall RRP replenishment process in that there is no corresponding decrement in either the rate at which vesicles are prepared for release during the initial several seconds of heavy use, or in the kinetics of the slower vesicle trafficking mode itself. In addition, there appears to be no defect in the machinery responsible for triggering exocytosis of vesicles that are ready for release. The onset of fatigue is dosage dependent as synapses of mice lacking both synapsin II alleles fatigue more quickly than synapses lacking only a single one. Schaffer collateral synapses lacking synapsin I have a more modest defect in this regard, although some types of inhibitory synapses may be affected more severely (Terada et al, J. Cell Biol. 145:1039-48 (1999)).

What is the mechanism for fatigue in the RRP replenishment process? A recent report has suggested that the vesicles that are prepared for release via the faster trafficking mode might be recycled locally at the active zone via fast "kiss and run" exo/endocytosis, and that the slower mode reflects recruitment of vesicles from the classically studied reserve/recycling pools that reside in the interior of the terminals (Pyle et al, Neuron. 28:221-31 (2000)). This model does not fit well with the kinetics reported here and elsewhere (Stevens et al, Neuron 24:1017-28 (1999), Stevens et al, Neuron 21:415-24 (1998)), however, because reserve vesicles take seconds and not minutes to be prepared for release (Pyle et al, Neuron. 28:221-31 (2000)). Instead, the rate of reserve vesicle mobilization matches better with the kinetics of the faster trafficking mode (compare the time constant of 6 s reported here to the time constant of 7 s for the mobilization of fluorescently labeled reserve vesicles reported in Pyle et al, Neuron. 28:221-31 (2000).

A model that elegantly incorporates the cell biological findings with several recently reported kinetic properties of synaptic physiology is that synapsins control the onset of synaptic fatigue by determining the size of a functional reserve pool of vesicles. Although the kinetics of fatigue onset and recovery are incompatible with the classic idea that the number of vesicles within the reserve pool determines the RRP replenishment rate by a massed action mechanism (Stevens et al, Neuron 24:1017-28 (1999)), synaptic terminals might be forced to switch to the slow mode of vesicle preparation for release after they had exhausted their standing supply of reserve vesicles (see FIG. 1). The slow mode would then represent the time it takes for used vesicles to complete the exo/endocytic cycle—a process involving several potentially slow steps including: endocytosis of the membrane (Ryan et al, Neuron 11:713-24 (1993), Ryan et al, Proc. Natl. Acad. Sci. USA 93:5567-71 (1996), Murthy et al, Nature 392:497-501 (1998)), reconstitution into usable vesicles, and—since partially filled vesicles apparently do not undergo exocytosis—refilling with neurotransmitter (Naito et al, J. Neurochem. 44:99-109 (1985)). Synapses with larger reserve pools would thus be able to draw on the reserve store for longer periods when used heavily. Conversely, the mutant terminals would fatigue faster if they started with smaller reserve pools that were expended sooner, after which the synapses would resort to releasing freshly packaged neurotransmitter from the recycling vesicles as they slowly became available.

Consistent with this idea, several studies have indicated that synapsins do regulate an intraterminal store of vesicles (Greengard et al, Science 259:780-5 (1993), Chi et al, Nat. Neurosci. 4:1187-93 (2001), Mozhayeva et al, J. Neurosci. 22:654-65 (2002)). Also consistent is the observation that it takes a similar amount of presynaptic stimulation to drive the synapses into their most fatigued state as it does to elicit the exocytosis of all of the reserve vesicles at least once Ryan et al, Proc. Natl. Acad. Sci. USA 93:5567-71 (1996)), and, the time constant of the slower trafficking mode (60 s) is similar to the characteristic time required for vesicles to travel all the way through the exo/endocytic cycle Ryan et al, Neuron 11:713-24 (1993).

The machinery needed for controlling the size of a functional reserve pool is present within presynaptic terminals making regulation of synaptic fatigue a potentially dynamic process. It has recently become clear that there is a large inert pool of vesicles within synaptic terminals that normally do not participate in the exo/endocytic cycle, even during episodes of extensive, heavy use (Harata et al, Trends Neurosci. 24:637-43 (2001)). Already, certain peptide growth factors have been implicated in eliciting intraterminal second messenger cascades that might liberate vesicles from this inert store by phosphorylating synapsins (Jovanovic et al, Nat. Neurosci. 3:323-9 (2000)).

EXAMPLE II

Experimental Details

Experiments were performed on 400 μm thick transverse hippocampal slices (with area CA3 removed) of two to three week old mice. Briefly, all synaptic responses were measured from patch clamped neurons held in whole cell voltage clamp mode. The extracellular recording solution contained (in mM) 120 NaCl, 1.25 $NaH_2PO_4$, 26 $NaHCO_3$, 10 glucose, 3.5 KCl, 2.6 $CaCl_2$, 1.3 $MgCl_2$, picrotoxin (50 μM), and D (−) APV (50 μM). The intracellular solution contained (in mM) 130 Cs-gluconate, 5 CsCl, 5 NaCl, 2 $MgCl_2$, 2 MgATP, 0.2 LIGTP, 1 EGTA, 0.2 $CaCl_2$, and 10 HEPES. Preparations were always allowed at least 4 minutes of rest before each experiment was initiated. Data were only accepted if the access resistance did not change throughout individual trials, and also between trials for the experiments documented in FIG. 6. Stimulation was conducted with a monopolar silver/silver chloride electrode inserted into a glass pipette (tip diameter>10 μm) and filled with recording solution. Synaptic strength during intense stimulation was measured as the slope of the rising phase of the postsynaptic response trace (30-60% of peak). As synaptic responses took longer than 30 ms to decay completely, measurements of synaptic potentials recorded at 35 Hz were adjusted for the slope of the baseline response over the 5 ms that preceded the stimulus artifact (less than 10% of total measure). Minimal stimulator settings were determined during low frequency stimulation as the strength needed to evoke successful synaptic transmission about half of the time or less. To make sure that transmission failures did not result from nerve conduction failures arising from axonal threshold fluctuations, minimal intensities were only used if it was possible to both increase and decrease the stimulus intensity by several percentages without changing the probability of release noticeably.

Results

Figure 5A:
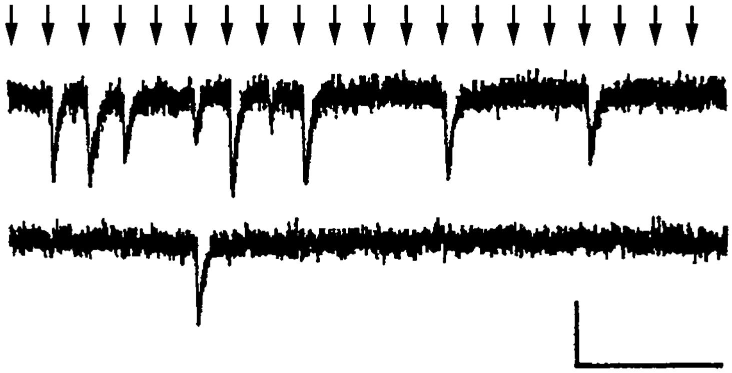
FIGS. 5A-5E. Synaptic terminals have a low steady state rate of release during 20 Hz use. A minimal number of Schaffer collaterals were stimulated at 20 Hz for 90 s.
Figure 5B:
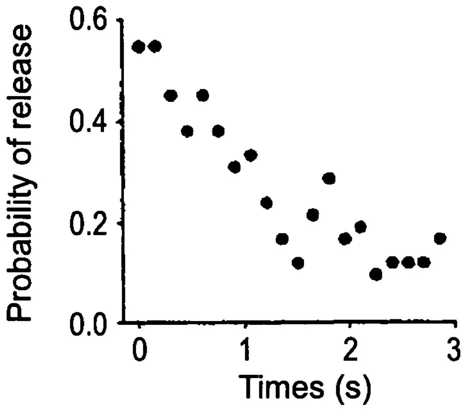
Figure 5C:
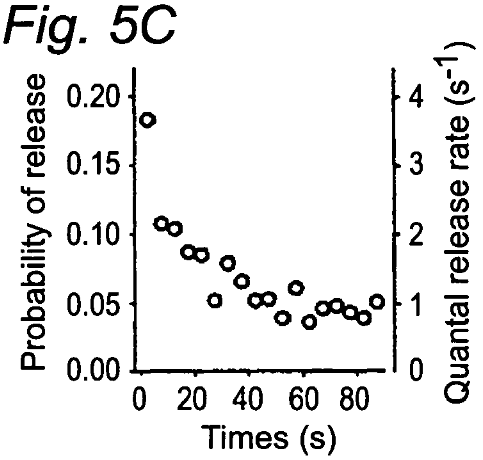

The main result is displayed in FIGS. 5A and 5C. CA1 pyramidal neurons were patch clamped in mouse hippocampal slices, and minimal numbers of afferent Schaffer collateral terminals were activated at 20 Hz for 90 s. The probability of release started off at a typical value for single synapses of 0.5, but after 1000 stimuli, it had depressed to 0.045 (FIG. 5C). Since action potentials were evoked at 20 Hz, this is equivalent to an overall release rate of 0.9 quanta per second (0.045 multiplied by 20 Hz). As the stimulation protocol may have activated more than one synapse, this represents an upper bound estimate of the steady state quantal rate of release at individual synapses when activated at 20 Hz.

Figure 5D:
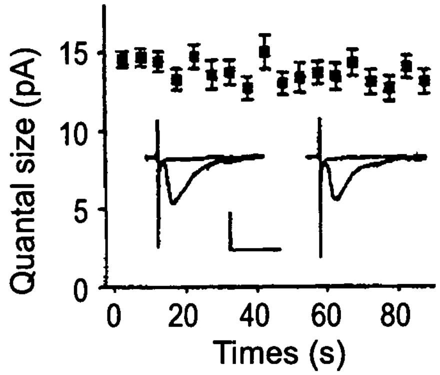

The steady state release rate was substantially lower than the initial release rate during the first several seconds of stimulation; i.e. on average, 8.9 quanta were released during the first one second. The decrement in the probability of release was due to short-term depression as the synaptic efficacy subsequently recovered during 4 minutes of rest (Zucker, Annu. Rev. Neurosci. 12:13-31 (1989)). The sizes of the successful postsynaptic responses did not decrease during stimulation, indicating that the depression was presynaptic in origin (FIG. 5D).

Figure 5E:
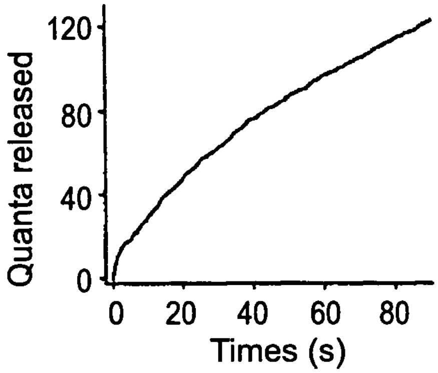

On average, the synaptic terminals activated in these experiments released a total of 123 quanta (FIG. 5E) during 90 s of stimulation. This would represent approximately three rounds of exocytosis of a cycling pool (the initial pool, plus two recycling rounds) consisting of 40 vesicles, each taking 45 s to travel through the exo/endocytic cycle one time—a scenario that is remarkably consistent with independent measures of the size of the cycling pool (Harata et al, Proc. Natl. Acad. Sci. USA 98(22):12748-12753 (2001)), and the time it takes for vesicles to be recycled by classically defined mechanisms (Ryan et al, Neuron 11(4):713-724 (1993)).

20 Hz Stimulation Drives Exocytosis at the Maximal Steady State Rate

20 Hz stimulation has been shown to be sufficiently rapid to drive the exocytosis of neurotransmitter near the maximum rate for some types of excitatory synaptic terminals (Abbott et al, Science 275(5297):220-224 (1997), Tsodyks and Markram, Proc. Nat. Acad. Sci. USA 94(2):719-723 (1997)). If this is also the case for Schaffer collateral synapses, then more rapid stimulation protocols should not elicit a higher exocytic rate. Synaptic strength was thus monitored during repetitive stimulation at both 20 and 35 Hz.

Since the purpose of these experiments was to compare release rates at times when the probability of release was substantially depressed, a higher intensity stimulus was used in order to simultaneously activate multiple afferent axons. Although it is often difficult to resolve the quantal content of the resulting postsynaptic responses during this sort of stimulation, the responses at individual Schaffer collateral synapses do sum linearly under the conditions of this type of experiment, allowing the composite response to be used as a linear proxy for transmitter release.

While the response sizes depressed more extensively over 90 s of stimulation at 35 Hz than at 20 Hz (FIGS. 6A & 6B), the overall rate of exocytosis (FIG. 6C—obtained by multiplying the synaptic strength by the stimulation frequency) was initially higher at the higher frequency. This difference was expected during the first several seconds because a few of the cycling vesicles in each terminal are known to accumulate in a readily releasable state (i.e., the readily releasable pool) during rest intervals such as the ones preceding these experiments, and the vesicles in this state can be triggered to undergo exocytosis quickly, at a rate that depends primarily on the frequency of stimulation.

After the first several seconds of stimulation, however, the overall rate of transmitter release reached a similar level at both frequencies (FIG. 6C). This indicates that 20 Hz stimulation is rapid enough to expend the readily releasable pool of vesicles within a few seconds. Thereafter, the rate of release no longer depends upon the stimulation frequency because it is determined by the processes controlling how long it takes for vesicles that were originally not in the releasable state (i.e., reserve vesicles)—or for ones completing the exo/endocytic cycle—to become available for action potential triggered exocytosis.

The rate of release elicited by both stimulus trains subsequently depressed substantially over the next 30 s, possibly reflecting depletion of the entire original supply of cycling vesicles (Zucker, Annu. Rev. Neurosci. 12:13-31 (1989), Ryan et al, Neuron 11(4):713-24 (1993); see also Stevens and Wesseling, Neuron 24(4):1017-1028 (1999)). The release rate depressed similarly at the two frequencies (FIG. 6D), eventually achieving a similar low steady state (steady state release rate was only 7.6% higher at 35 Hz compared to 20 Hz). As the more rapid stimulation did not elicit much more exocytosis, this result indicates that continuous 20 Hz stimulation is indeed sufficient to elicit transmitter release from Schaffer collateral terminals at close to the maximum rate. The steady state value of less than one exocytic event per synapse per second measured above must thus be close to the maximum release rate at those synapses during exhaustive use.

Estimated Maximal Quantal Release Rate at Larger Populations of Synapses

Although the minimal stimulus technique used above to monitor exocytic events at individual or small numbers of synaptic terminals is potentially biased towards synapses with a high initial probability of release and a large quantal size, the experiments conducted at the higher stimulus intensity avoided this problem because the responses were generated from the simultaneous activation of a larger population of synapses; the initial synaptic strength averaged 342 pA indicating about 75 synapses were activated simultaneously—given a quantal size of 13.5 pA (FIG. 5D) and an average initial probability of release for these synapses of 0.35 (Huang and Stevens, J. Neurophysiol. 78(6):2870-2780 (1997) and references therein). The sizes of the responses recorded during the 20 Hz stimulation depressed to 9.0% of their original value after 1000 action potentials—a reduction that was equivalent to the corresponding depression in the probability of release (also to 9.0%, FIGS. 5B & 5C) observed during minimal stimulation. This indicates that the average probability of release at these synapses depressed to about 0.031 at 20 Hz (obtained by multiplying the average initial probability of release (0.35) by the residual synaptic strength of 9.0%). This corresponds to a quantal release rate for typical synapses that is also less than one event per second (i.e. 0.62/s-0.031 multiplied by 20 Hz), confirming that the maximal rate of release at Schaffer collateral terminals is extremely low during exhaustive use.

Together, these results indicate that the maximum rate of transmitter release from individual Schaffer collateral terminals is less than one quantum per second during exhaustive use, although when well rested, these synapses can transiently release transmitter at much higher rates during sporadic bursts of activity. Since these terminals apparently only make use of several dozen of their synaptic vesicles, the low rate during exhaustive use corresponds to the steady state, rate that would be expected if synaptic vesicles were recycled slowly as measured previously with several optical tracer techniques ((Ryan et al, Neuron 11(4):713-24 (1993) and references therein).

The contents of all documents and other information sources cited above are incorporated herein by reference.

What is claimed is:

1. A method of identifying a candidate anti-epileptic agent comprising screening test compounds for their ability to modulate the number of synaptic vesicles at excitatory synapses that are functionally available to participate in synaptic transmission during an episode of repetitive synaptic use, wherein a test compound that reduces the number of said synaptic vesicles is a candidate anti-epileptic agent.

2. The method according to claim 1 wherein the number of said synaptic vesicles is determined optically.

3. The method according to claim 1 wherein the number of said synaptic vesicles is determined biochemically.

4. The method according to claim 1 wherein said method is effected using cultured neurons.

5. The method according to claim 4 wherein said neurons are harvested from a mammal transgenically altered to express synapto-pHluorins.

6. The method according to claim 4 wherein the number of synaptic vesicles is determined by a method comprising transfecting said neurons with a nucleic acid encoding a protein that is targeted to synaptic vesicles and that fluoresces when synaptic vesicles undergo exocytosis.

7. The method according to claim 4 wherein said synaptic vesicles are labeled with an externally applied dye during a period when said synaptic vesicles undergo endocytosis.

8. The method according to claim 1 wherein the number of said synaptic vesicles is determined by a method that comprises measuring the amount of neurotransmitter that is released upon depolarization, wherein a test compound that reduces the number of said synaptic vesicles reduces the amount of neurotransmitter released.

9. The method according to claim 8 wherein said neurotransmitter is glutamate.

10. A method of identifying a candidate anti-epileptic agent comprising screening test compounds for their ability to modulate the number of synaptic vesicles at excitatory synapses, but not at inhibitory synapses, that are functionally available to participate in synaptic transmission during repetitive synaptic use, wherein a test compound that reduces the number of said synaptic vesicles at excitatory synapses, but not at inhibitory synapses, is a candidate anti-epileptic agent.

11. A method of identifying a candidate anti-epileptic agent comprising screening test compounds for their ability to modulate the number of synaptic vesicles differentially at excitatory versus inhibitory synapses that are functionally available to participate in synaptic transmission during repetitive synaptic use, wherein a test compound that reduces the number of said synaptic vesicles differentially at excitatory versus inhibitory synapses is a candidate anti-epileptic agent.

* * * * *